US00PP10392P

United States Patent [19]

Plate

[11] Patent Number: Plant 10,392

[45] Date of Patent: May 12, 1998

[54] PHALAENOPSIS ORCHID PLANT NAMED 'ABYLOS'

[75] Inventor: Renate Plate, Bremen, Germany

[73] Assignee: Wolfgang Bock, Pflanzenexport KG, Bremen, Germany

[21] Appl. No.: 743,070

[22] Filed: Nov. 4, 1996

[51] Int. Cl.[6] ..... A01H 5/00

[52] U.S. Cl. ..... Plt./87.3

[58] Field of Search ..... Plt./87.3

*Primary Examiner*—James R. Feyrer
*Assistant Examiner*—Elizabeth C. Kemmerer
*Attorney, Agent, or Firm*—Foley & Lardner

[57] ABSTRACT

A new and distinct *Phalaenopsis* orchid variety named 'Abylos' particularly characterized by its abundant white flowers which are flushed with pink, and a contrasting dark purple center. Its horticultural traits further include economical propagation via tissue culture, very rapid growth, abundant flower production, and plant dimensions suitable for packaging and shipping to market.

2 Drawing Sheets

The present invention comprises a new and distinct cultivar of *Phalaenopsis*, a genus in the family Orchidacease, referred to by the cultivar name 'Abylos'. The new cultivar is a hybrid selected from the progeny of a cross of parent plants identified below.

*Phalaenopsis* comprise a genus of about 55 species of herbaceous perennials many of which, or the hybrids thereof, are suitable for cultivation in the home or greenhouse. *Phalaenopsis* are predominantly epiphytic or rock-dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade, or sold as flowering potted plants for home or interiorscape.

*Phalaenopsis* produce upright or pendent lateral racemes, often with many showy flowers which open in succession beginning with the lowermost. The flowers possess three sepals, and three petals, the lateral ones being alike. The lowermost petal, called the labellum, is three lobed and is often more brightly colored than the other flower segments. Flower colors include various shades of pink, white, yellow and red-brown.

*Phalaenopsis* orchids are typically propagated from seeds. However, plants of *Phalaenopsis* are capable of being asexually reproduced from off-shoots which frequently arise from the lower bracts of the inflorescence. The resulting plants are detached from the mother plant and may be planted in a suitable substrate. Asexual propagation of *Phalaenopsis* can also be performed by tissue culture, although this technique is not widely practiced commercially because it is often relatively inefficient and costly as currently applied.

The new cultivar is a product of a breeding program carried out by the inventor Renate Plate in Bremen, Germany. The new cultivar 'Abylos' is a result of a cross of selected, but unnamed parentage made by the inventor in Bremen, Germany in 1988. The new cultivar was discovered from the progeny of the stated cross by the inventor in Bremen, Germany in October 1990. Asexual propagation by tissue culture done under the supervision of the inventor in Bremen, Germany was used to increase the number of plants for evaluation and has demonstrated the stability of the combination of characteristics from generation to generation.

The following observations, measurements and values describe plants grown in Lake Worth, Fla. under greenhouse conditions which closely approximate those generally used in horticultural practice.

The following traits have been repeatedly observed to be characteristics which in combination distinguish 'Abylos' from generally available seedling-derived *Phalaenopsis* common in commercial cultivation.

1. The flowers produced by 'Abylos' are white flushed with light pink with a contrasting dark purple center.
2. 'Abylos' is a particularly abundant bloomer.
3. The inflorescence produced by 'Abylos' is short, oftern branched, and easily staked and packaged for shipping.
4. Plants of 'Abylos' grow very quickly, producing marketable flowering plants in approximately 9–11 months.
5. Plants of 'Abylos' may be propagated economically and uniformly using tissue culture.

It is difficult to compare the new cultivar with commercially available seedling-derived *Phalaenopsis* which are heterogeneous genetically, and typically lack uniformity in growth vigor, habit, and flower quality. Because of these inconsistent characteristics, a direct comparison for 'Abylos' is not possible. 'Abylos' is a single genotype asexually propagated via tissue culture, and its combined horticultural properties listed above are uniform and predictable.

All color references are measured against The Royal Horticultural Society color chart. Colors are approximate as color depends on horticultural practices such as light level and fertilization rate, among others, without, however any change in genotype.

In the color photographic drawings, the photograph on Sheet 1 comprises a top perspective view of the inflorescence and foliage of a group of plants of 'Abylos' in 10.2 cm pots. The photograph was taken approximately 12 months after planting 16 week old liners obtained by tissue culture and grown under appropriate growing conditions.

The photograph on Sheet 2 is a close up view of the flowers.

Colors are as accurate as possible with color illustrations of this type.

Origin: Seedling from a cross of selected, but unnamed parentage.

Classification: *Phalaenopsis hybrid*, cv. 'Abylos'.

Propagation: Asexual propagation by tissue culture.

Inflorescence:

*Flower description.*—The sepals and petals are white flushed with light pink. The lateral (lower) sepals are also suffused with minute dark pink speckles near their base. The sepals are elliptic-ovate in shape, the lateral petals are broadly ovate. The sepals and petals are slighlty cupped. The labellum is deeply three-lobed with two prominent callosities at the central junction of the lateral lobes and base of the midlobe. The lateral lobes of the labellum fold upward about the column, the midlobe extends forward and is terminated by two twisted filiform appendages at the apex. The lateral lobes of the labellum are obovate in shape, the midlobe is triangular. The labellum is dark purple with a white center which is spotted and striped with dark red, the two callosities are yellow with minute dark red spots.

*Dimension.*—Overall: Approximately 7.2 cm to 7.8 cm wide, and 6.6 to 7.3 in height. Sepals: Approximately 3.3 cm to 3.8 cm long, and 2.1 cm to 2.4 cm wide. Petals: Approximately 3.5 cm to 3.8 cm long, and 3.4 cm to 3.8 cm wide. Labellum: Approximately 2.2 cm to 2.4 cm long, and 2.1 cm wide (not flattened).

*Flower color.*—Sepals: Adaxial surface: 155 D to 69 D, lower sepals speckeld with 60 B-C. Abaxial surface: 69 B-C. Lateral Petals: Adaxial surface: 155 D to 69 D, flushed with 84 B. Abaxial surface: 155 D to 69 D. Labellum: Adaxial surface: Central area white striped and speckled with 60 A. Callosities: 13 A, speckled with 60 A. Lateral lobes: 78 A-B, with 178 C and 155 D on margins. Midlobe: 78 A, and 178 B. Abaxial surface: All three segments, central areas 155 D, darkening to 72 B, tinged with 178 C at margin. Raceme: Dimension: The raceme is typically staked upright to a height of approximately 45 cm. The racemen is approximately 55 cm from base to tip, and 0.5 cm in diameter at its midpoint. The raceme is 200 B, 187 A in color.

*Flowering time.*—For untreated plants as depicted in the photograph on Sheet 1 and which are flowering for the second time, 8–10 flowers/unopened buds are present. First flowers can be expected approximately 4–6 months after planting a 16 week old liner; approximately 4–5 flowers are present.

Reproductive organs: The stamens, style and stigmas are fused into a single short column, possessing one terminal anther with pollen grains united into a pollinia, which are covered by an anther cap. The stigma is located under the column behind the pollinia. Ovary inferior, three carples present.

*Column.*—The column is approximately 9.5 mm long, 6 mm wide, and is 82 B, 155 D in color.

*Pollinia.*—Two 1.1 mm oval masses of pollen present, 23 A in color. Viscidium present.

*Stigma.*—Concave, sticky oval 4 mm–5 mm area under column, 155 D in color.

*Ovary.*—13 mm long, 2.5 mm diameter, color 84 C. Pedicel approximately 2.5 cm to 2.8 cm long, 3.0 mm diameter; lighter and greener than but closest to 186 D.

General appearance: Under appropriate growing conditions, plants of 'Abylos' (excluding raceme) attain a mature size of approximately 10.0 cm to 16 cm in height and approximately 33 cm to 38 cm in width.

*Leaves.*—Form: The leaf blade is long and elliptic to obovate with an obtuse to slightly retuse apex and a cuneate base. The margins are entire. The midrib is straight over the length of the leaf. The leaf blade is folded upward from the midrib. The leaf is often curved downward. The upper leaf surface is slightly glossy, more so on newly emerged leaves. The leaves are leathery, and thick. Size: Leaf blades of a matrue sized plant are approximately 22 cm to 27 cm in length and approximately 5.8 cm to 6.2 cm in width. Veins: Veins are sunken, within the thick leaf blade. Color: Adaxial surface: Lighter and greener than, but closest to 137 A. Abaxial surface: 146 B, often tinged with anthiocyaneous 59 A.

*Roots.*—Very thick greenish white fleshy roots.

GENERAL OBSERVATIONS

*Phalaenopsis* 'Abylos' is a particularly abundant bloomer having flowers which are white flushed with light pink and a contrasting dark purple center. The inflorescence is short, often branched and easily packaged for shipping. The plant grows very quickly to marketable size. 'Abylos' can be economically propagated via tissue culture.

I claim:

1. A new and distinct cultivar of *Phalaenopsis* Orchid plant named 'Abylos', as illustrated and described.

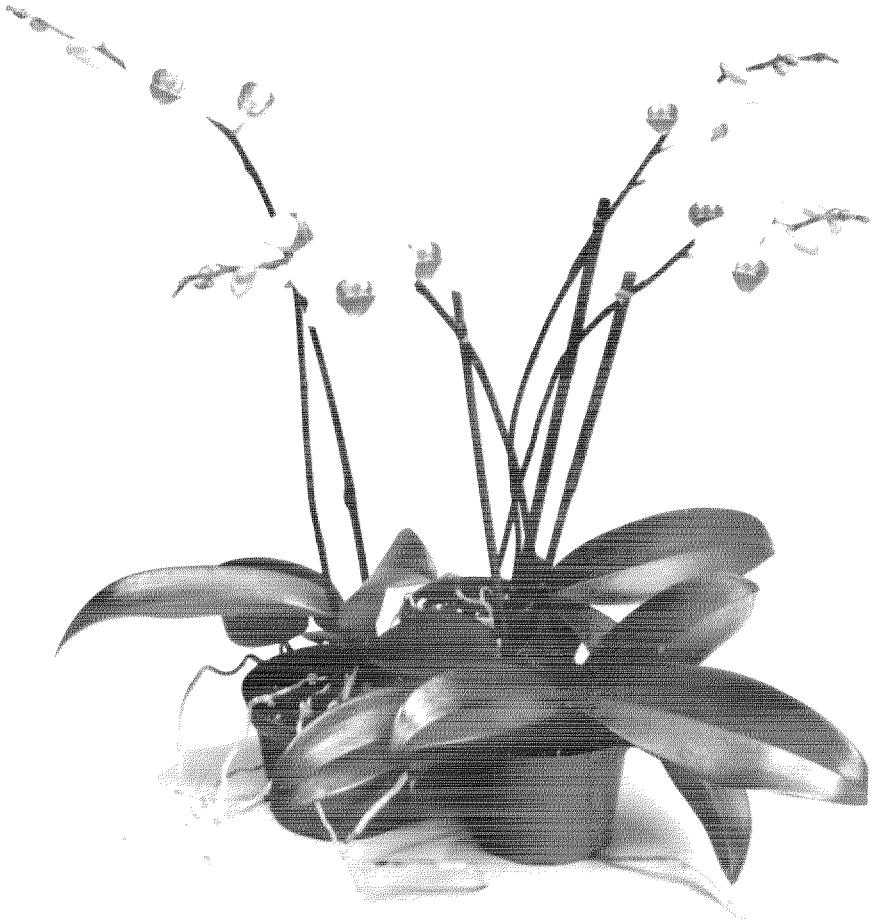

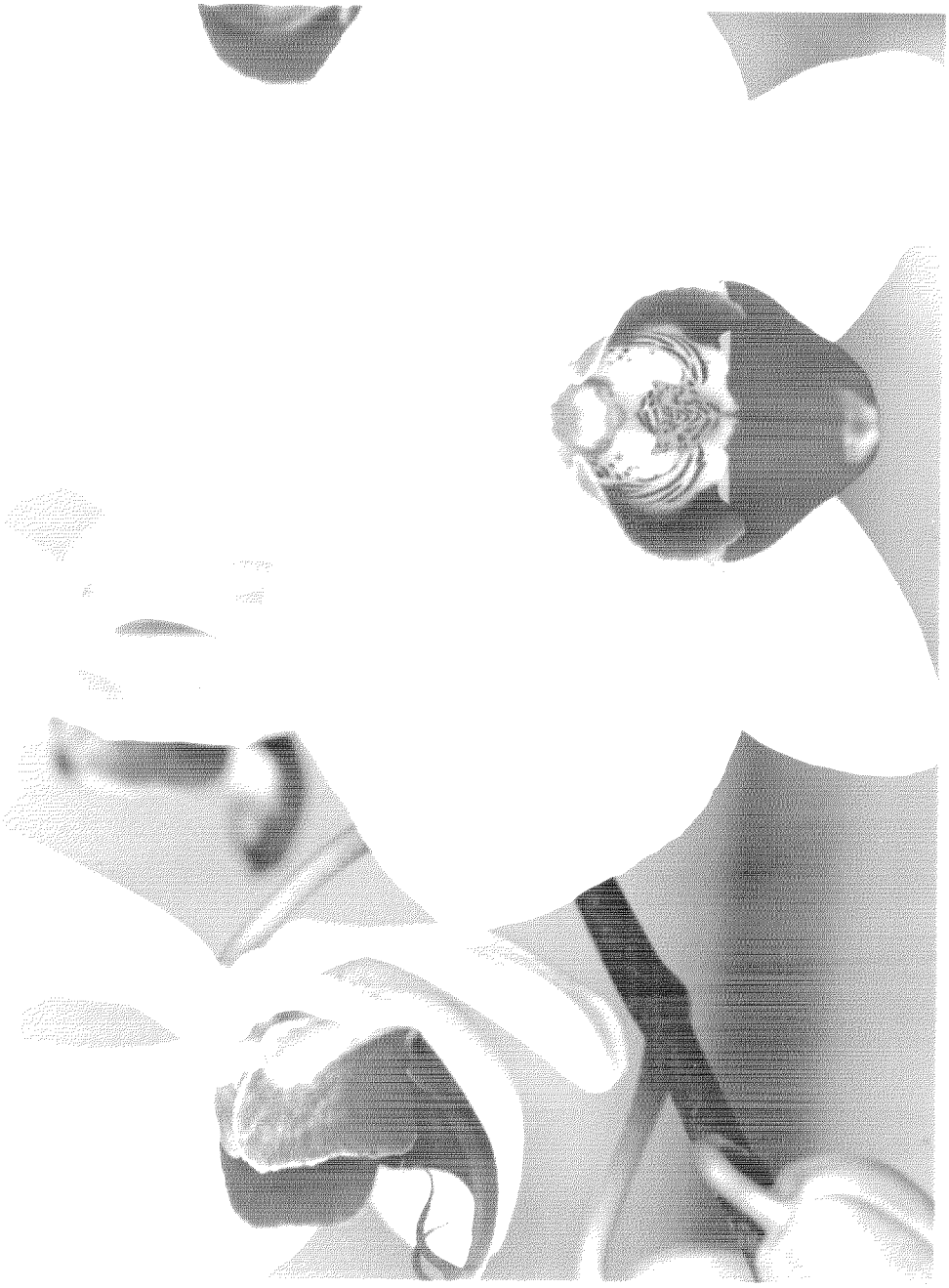

* * * * *